United States Patent [19]

Cielo et al.

[11] Patent Number: 4,972,091

[45] Date of Patent: Nov. 20, 1990

[54] METHOD AND APPARATUS FOR DETECTING THE PRESENCE OF FLAWS IN A MOVING SHEET OF MATERIAL

[75] Inventors: Paolo Cielo; Marc Dufour, both of Montreal; Ghislain Vaudreuil, Boucherville, all of Canada

[73] Assignee: Canadian Patents and Development Limited/Societe Canadienne des Brevets et D'Exploitation Limitee, Ottawa, Canada

[21] Appl. No.: 352,197

[22] Filed: May 16, 1989

[51] Int. Cl.$^5$ ............................................. G01N 21/88
[52] U.S. Cl. .................................... 250/562; 356/430
[58] Field of Search ............... 250/562, 563, 572, 225; 356/430, 431, 369

[56] References Cited

U.S. PATENT DOCUMENTS

| | | | |
|---|---|---|---|
| 3,783,296 | 1/1974 | Blevins | 250/550 |
| 3,804,529 | 4/1974 | Hansler | 356/167 |
| 3,984,189 | 10/1976 | Seki et al. | 356/73 |
| 3,989,387 | 11/1976 | Hategan | 250/237 |
| 4,162,126 | 7/1979 | Nakagawa et al. | 356/237 |
| 4,223,346 | 9/1980 | Neiheisel et al. | 358/106 |
| 4,314,763 | 2/1982 | Steigmeier et al. | 356/237 |
| 4,465,371 | 8/1984 | Pernick | 356/237 |
| 4,482,250 | 11/1984 | Hirvonen | 256/369 |
| 4,506,980 | 3/1985 | Pryor et al. | 356/237 |
| 4,559,451 | 12/1985 | Curl | 250/563 |
| 4,585,348 | 4/1986 | Chastang | 356/369 |
| 4,619,527 | 10/1986 | Leuenberger et al. | 356/238 |
| 4,629,319 | 12/1986 | Clarke et al. | 356/237 |
| 4,632,546 | 12/1986 | Sick et al. | 356/237 |
| 4,668,860 | 5/1987 | Anthon | 250/225 |

Primary Examiner—David C. Nelms
Assistant Examiner—Sherrie Hsia
Attorney, Agent, or Firm—Foley & Lardner, Schwartz, Jeffery, Schwaab, Mack, Blumenthal & Evans

[57] ABSTRACT

The present disclosure describes an apparatus and a method for detecting the presence of flaws in a moving sheet of material. The apparatus comprises a light source for projecting a light beam; a beam shaping unit for shaping the light beam into a predetermined structured light pattern, and projecting the structured light pattern onto a portion of the surface of the sheet; an optical unit for collecting light emitted from the portion of the surface; and a light detecting unit for receiving the light collected by the optical unit and generating an electrical signal indicative of the intensity of the light generated from the portion of the surface. A signal processing unit is provided for filtering the electrical signal, the signal processing unit having predetermined characteristics specifically adapted to match an expected electrical signal corresponding to the predetermined structured light pattern. The present invention can be used in a transmission mode wherein the light beam is projected onto one side of the moving sheet and detected from the opposite side, or in a reflective mode wherein the light beam is projected onto and detected from the same side of the moving sheet.

12 Claims, 4 Drawing Sheets

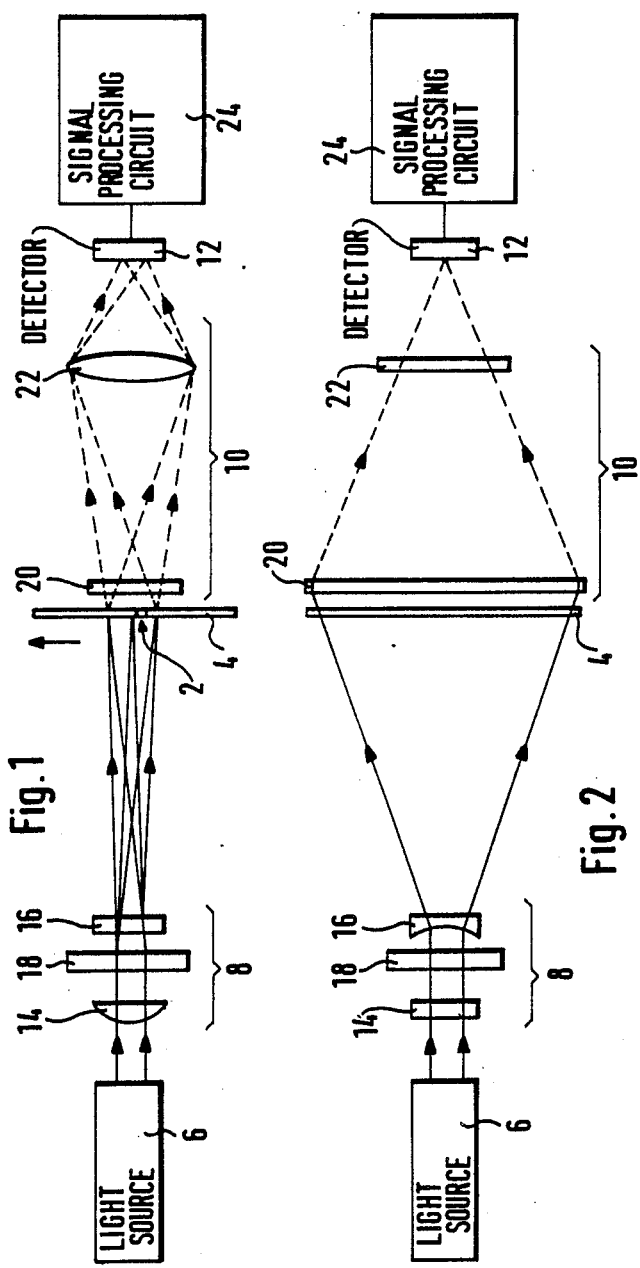

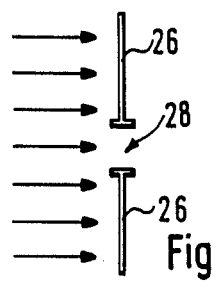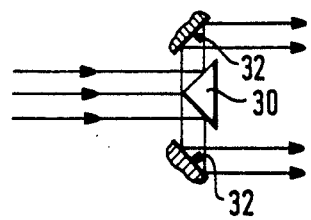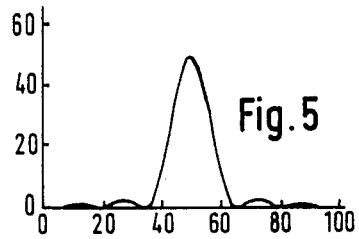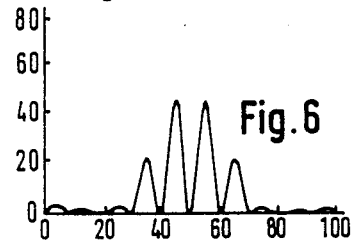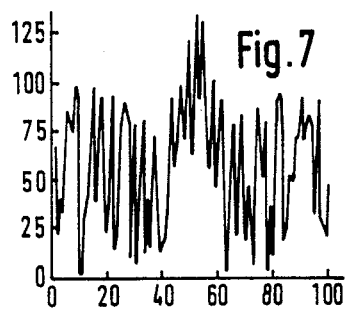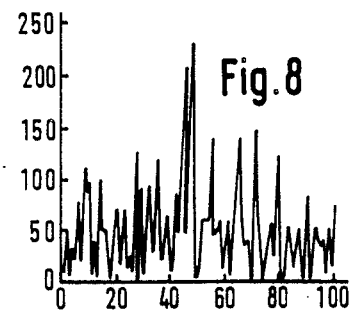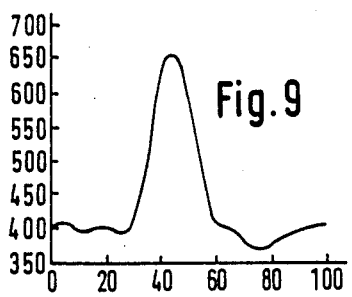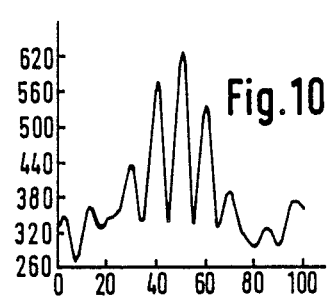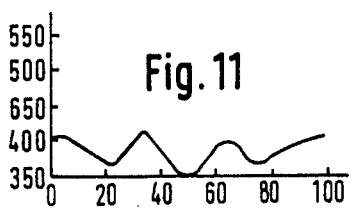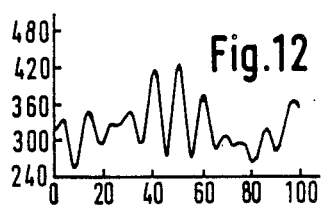

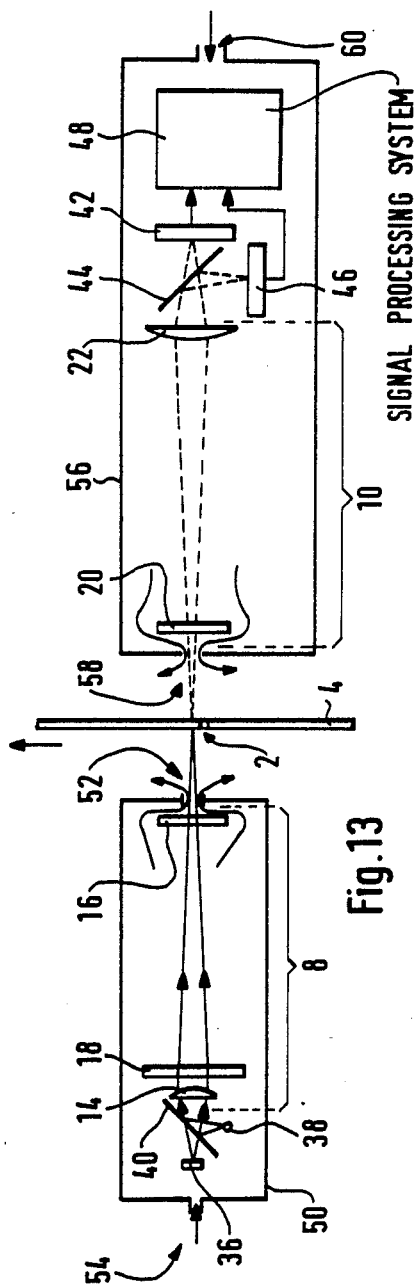
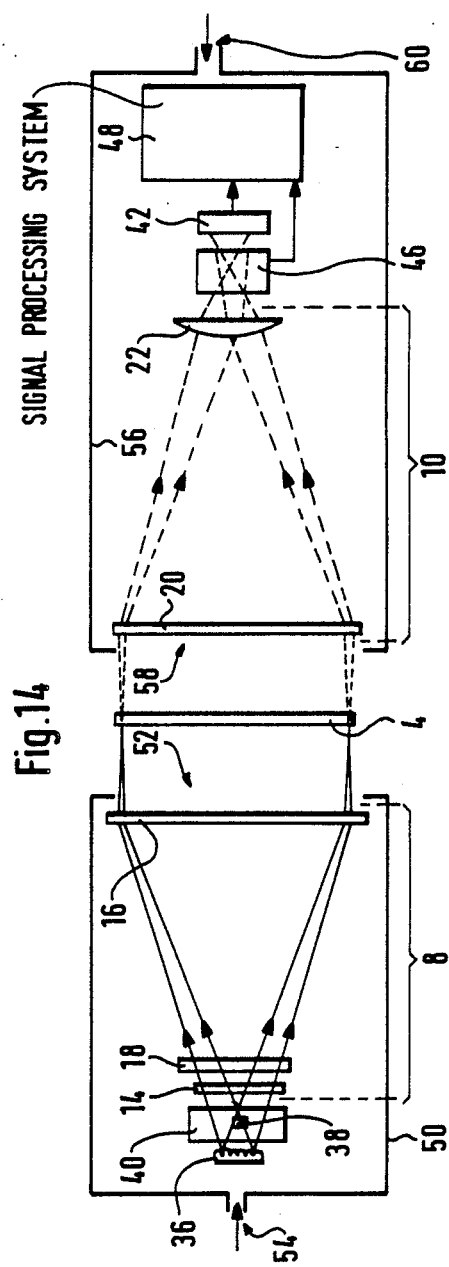
Fig.13
Fig.14

METHOD AND APPARATUS FOR DETECTING THE PRESENCE OF FLAWS IN A MOVING SHEET OF MATERIAL

FIELD OF THE INVENTION

This invention generally relates to inspecting apparatus and method for detecting the presence of flaws in a moving sheet of material.

BACKGROUND OF THE INVENTION

The optical detection of small defects such as pinholes in continuously-produced sheets of materials such as aluminum foil, polymer films or paper is an important requirement for many materials processing industries.

In some cases, such as in the production of sealed metallic foils for food containers or in the production of plastic films for electric-insulation applications, the product must be guaranteed defect-free so that a 100% inspection is required. In other cases, an automated sampling procedure may be applied to determine the trends in the average density of pinholes across the product for statistical quality control and process monitoring requirements.

Pinholes in insulating materials are sometimes detected by electric-conductance devices using high-voltage brushes or sponges in contact with both sides of the sheet for pinhole detection through the establishment of spark discharges between the electrodes. Such techniques are often unreliable, low-speed, and subject to wear and erosion problems. Another approach is by liquid or gaseous leak testing on the assembled container. This approach is quite expensive in its implementation and in any case cannot be used by the sheet-producing company which must guarantee a pinhole-free sheet product to the container-manufacturing company.

Optical inspection techniques have been increasingly used for these applications in the last years. Optical methods are attractive because they are noncontact and thus easy to implement and rapid to scan over large sheets moving at high speed. A typical known apparatus for the optical detection of relatively large pinholes comprises a video camera used to image the moving sheet which is to be inspected. Backside flash illumination may be used to localize the pinhole position in fast-moving sheets with good spatial resolution. The camera may alternatively be situated on the same side as the illumination source to detect defects which do not correspond to a perforation of the sheet.

This known approach is mainly useful for the detection of relatively large pinholes, of the order of 1 mm$^2$ in size. For the detection of very small pinholes, of the order of 10 $\mu$m in diameter, the camera must be equipped with a close-up lens of the microscope kind. Such objectives have a typical operating distance of a few mm and a numerical aperture (N.A.) of the order of 0.5 to resolve a pinhole diameter d of the order of 10 $\mu$m. This leads to a reduced field of view of less than 1 cm$^2$ and to a depth of field of the order of d/NA$\approx$20 $\mu$m, hardly compatible with typical industrial requirements where a 1 meter-wide sheet is being drawn at speeds of 10 m/s with transverse fluctuations of several mm of amplitude.

Another known technique includes the reduction of the spatial resolution requirements to extend the field of view and the depth of field. A standard camera objective is used to image an area of typically 1 m$^2$ with a 1 mm spatial resolution. This results in a depth of field of several cm, relaxing positioning requirements. However, defects smaller than 1 mm in size often escape detection unless a very strong illumination power is used to compensate for the low pinhole/pixel surface ratio.

Still another known technique includes spatial filtering under continuous illumination. A high-power continuous source is used for backside illumination of the moving sheet. The pinhole imaged during the camera integration time of 1/30 of a second will appear as a short line in the camera image. A sheet moving at 10 m/s will displace through 0.3 m during the camera integration time. Knowing the direction of the sheet movement, the camera image may be digitally filtered to enhance the visibility of lines oriented along such a direction. Again, spatial resolution considerations make this approach not sensitive to very small defects.

Concerning optical reflective techniques, there are two basic methods for reflective optical inspection systems: camera viewing under incoherent illumination, (using lamps, as in U.S. Pat. No. 4,162,126), or laser scanning (most often with rotating mirrors such as in U.S. Pat. No. 4,632,546). Incoherent illumination avoids speckle but it is affected by a number of problems including reduced illumination power density, limited depth of field, as well as long scanning time and difficulty to keep a convenient air purge over a large window aperture when a two-dimensional matrix-array camera is used. Laser scanning offers high instantaneous power, strong immunity to ambient light, long depth of field and convenient air purging through a slit, but it requires a delicate mechanical scanning device subject to long-term wear, it is subject to speckle noise, and requires a very high speed detector to resolve each pixel during a line scan.

It is an object of the present invention to provide apparatus and method for detecting the presence of flaws smaller than the flaws detected with known apparatuses and methods.

SUMMARY OF THE INVENTION

According to the present invention, there is provided an apparatus for detecting the presence of flaws in a moving sheet of material, comprising:
  a light source for projecting a light beam;
  beam shaping means for shaping said light beam into a predetermined structured light pattern, and projecting said strutured light pattern onto a portion of the surface of said sheet;
  optical means for collecting light emitted from said portion of said surface;
  light detecting means for receiving said light collected by said optical means, and generating an electrical signal indicative of the intensity of said light emitted from said portion of said surface;
  signal processing means for filtering said electrical signal, said signal processing means having predetermined characteristics specifically adapted to match an expected electrical signal corresponding to said predetermined structured light pattern; and
  signal detecting means connected to the output of said signal processing means for detecting the presence of flaws in said sheet.

According to the present invention, there is also provided a method for detecting the presence of flaws in a moving sheet of material, comprising the steps of:
  (a) projecting a light beam;

(b) shaping said light beam into a predetermined structured light pattern;

(c) projecting said predetermined light pattern onto a portion of the surface of said sheet;

(d) collecting light emitted from said portion of said surface;

(e) generating an electrical signal indicative of the intensity of said light collected during said step (d);

(f) filtering said electrical signal with a filter having predetermined characteristics specifically adapted to match an expected electrical signal corresponding to said predetermined structured light pattern; and (g) detecting the presence of flaws in said sheet from the output signal of said filter.

The objects, advantages and other features of the present invention will become more apparent upon reading of the following non restrictive description of preferred embodiments thereof, given for the purpose of examplification only with reference to the accompanying drawings.

BRIEF DESCRIPTION OF THE DRAWINGS

FIG. 1 illustrates in a side view an inspecting apparatus for detecting the presence of a hole in a moving sheet of material according to the present invention.

FIG. 2 illustrates in a view from above the apparatus shown in FIG. 1.

FIG. 3 illustrates in a side view a device that can be used in the beam shaping unit according to the present invention.

FIG. 4 illustrates in a side view a device that can be used in the beam shaping unit according to the present invention.

FIG. 5 shows the intensity distribution of the signal detected when the device shown in FIG. 3 is used.

FIG. 6 shows the intensity distribution of the detected signal when the device shown in FIG. 4 is used.

FIG. 7 shows the intensity distribution of FIG. 5 with noise.

FIG. 8 shows the intensity distribution of FIG. 6 with noise.

FIG. 9 shows the intensity distribution of FIG. 7 after filtering according to the present invention.

FIG. 10 shows the intensity distribution of FIG. 8 after filtering according to the present invention.

FIG. 11 shows the intensity distribution of the signal detected after filtering according to the present invention when the device of FIG. 3 is used while no hole is present in the sheet.

FIG. 12 shows the intensity distribution of the signal detected after filtering according to the present invention when the device of FIG. 4 is used while no hole is present in the sheet.

FIG. 13 illustrates in a side view another apparatus for detecting the presence of a hole in a sheet of material according to the present invention.

FIG. 14 illustrates in a view from above the apparatus shown in FIG. 13.

DETAILED DESCRIPTION OF THE DRAWINGS

Figure 15:
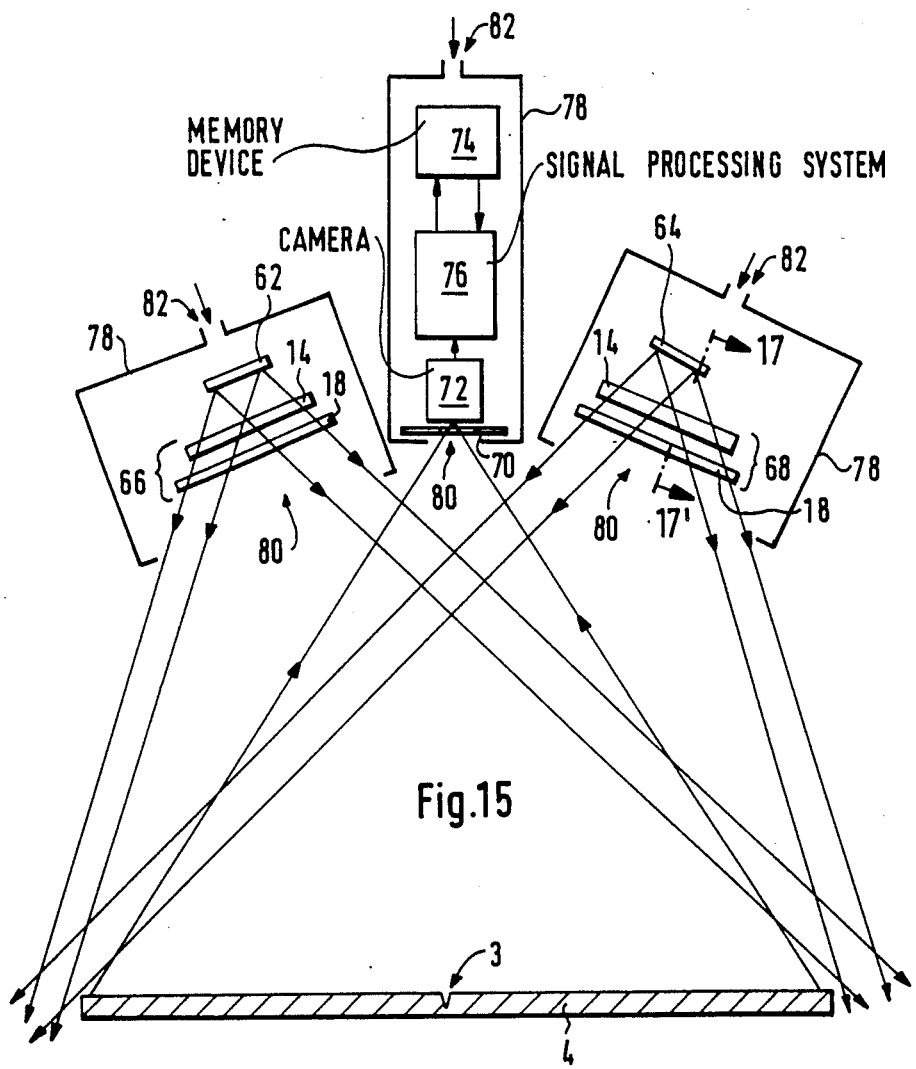
FIG. 15 illustrates an elevation of another apparatus for detecting flaws in a moving sheet of material according to the present invention.

Referring now to FIGS. 1 and 2, there is shown an apparatus for detecting the presence of a defect 2 in a moving sheet 4 of material. The apparatus comprises a coherent light source 6 for projecting a light beam. The light beam is shaped by a beam shaping unit 8 into a predetermined structured light pattern. The structured light pattern is projected onto a portion of the surface of the sheet 4. The apparatus also comprises an optical unit 10 for collecting light transmitted through the sheet 4 when a hole 2 is present in the sheet. A large size detector 12 receives the light collected by the optical unit 10 and generates an electrical signal indicative of the intensity of the light transmitted through the sheet 4 when a hole 2 is present. Other kinds of detectors can be used, such as a linear photodiode array with its axis oriented perpendicular to the direction of motion of the sheet.

The apparatus also comprises a signal processing circuit 24 including a filter for filtering the electrical signal generated by the detector 12. The filter has predetermined characteristics specifically adapted to match an expected electrical signal corresponding to the predetermined structured light pattern. The signal processing circuit also comprises a signal detector connected to the output of the filter for detecting the presence of a hole 2 in the sheet 4.

The beam shaping unit 8 comprises a first cylindrical lens 14 for converging the light beam in a direction parallel to the direction in which the sheet 4 moves as indicated by the arrow in FIG. 1. The beam shaping unit 8 also comprises a second cylindrical lens 16 for expanding the light beam in a direction substantially perpendicular to the direction in which the sheet 4 moves, and a device 18 for specifically shaping the light beam into a predetermined structured light pattern.

The optical unit 10 comprises a wide area lens 20 for collecting the light transmitted through the sheet 4 when a hole 2 is present in a direction substantially perpendicular to the direction in which the sheet 4 moves, and a cylindrical lens 22 for focusing the transmitted light onto the large size detector 12.

The projected beam pattern, which has typically a width of less than one millimeter in the direction parallel to the sheet movement, is expanded to a width of the order of one meter in the transverse direction by use of the second cylindrical lens 16. The full width of a relatively large sheet may thus be inspected with a single light source and detector, while the low signal level resulting from such a wide spread of the light beam is compensated by the efficient signal-extraction methods according to the present invention. The diverging beam is collected, when transmitted through pinholes, by the wide area lens 20. The wide area lens 20 can be a Fresnel lens which is compact, light-weight and inexpensive though providing limited image sharpness. Such a limited focusing power, as well as the divergence of the transmitted beam introduced by diffraction through the pinhole, can be accepted in the present configuration because of the large size of the detector. Similar considerations show that the depth of field extends in this case over several cm, making this apparatus easy to install and relatively insensitive to sheet flutter.

Referring now to FIG. 3, there is shown a device that can be used in the beam shaping unit for specifically shaping the light beam into a predetermined structured light pattern. The device comprises an opaque member 26 provided with a slit 28 having its axis oriented parallel to the plane of the sheet 4, and perpendicularly to the direction in which the sheet 4 moves.

Referring now to FIG. 4, there is shown another device that can be used in the beam shaping unit 8 for shaping the light beam into a predetermined structured light pattern. This device comprises a beam splitting device 30 for splitting the light beam into two secondary light beams, and reflecting surfaces 32 for superposing the two secondary light beams at an angle so that the structured light pattern, projected onto the surface of the sheet, contains interference fringes. Other light patterns can be produced using appropriate beam-shaping units.

Referring now to FIG. 5, there is shown the intensity distribution of the signal detected when the device shown in FIG. 3 is used. The vertical axis indicates the signal level, and the horizontal axis indicates the time in microseconds. A simple slit, oriented with its axis parallel to the sheet plane and perpendicular to the direction of the sheet movement, produces a characteristic sin x/x light distribution whose half-width is inversely proportional to the slit width. Similar light distributions can be obtained without blocking out part of the signal by using a transparent phase hologram of similar shape. Once the light pattern is known, the shape of the signal expected when a pinhole scans such a light pattern can easily be recognized even in the presence of substantial reflected-ambient-light or electronic noise.

Referring now to FIG. 6, there is shown the intensity distribution of the detected signal when the device shown in FIG. 4 is used. The vertical axis indicates the signal level, and the horizontal axis indicates the time in microseconds.

Referring now to FIGS. 7 and 8, there are shown respectively the intensity distributions of FIGS. 5 and 6 with noise. The vertical axis indicates the signal level, and the horizontal axis indicates the time in microseconds. A randomly or exponentially distributed, 1 MHz bandwidth noise has been added to the signal represented on FIGS. 5 and 6 to produce respectively the signal represented on FIGS. 7 and 8. The signal is hardly recognizable when the noise is introduced.

Referring now to FIGS. 9 and 10, there are shown respectively the intensity distributions of FIGS. 7 and 8 after filtering according to the present invention. The vertical axis indicates the signal level, and the horizontal axis indicates the time in microseconds. After filtering, the signal is effectively extracted from the noise as it can be seen on FIGS. 9 and 10. The filtering consists of a deconvolution of the signal plus noise traces with the expected electrical signal.

Referring now to FIGS. 11 and 12, there are shown respectively the intensity distributions of the detected signal after filtering according to the present invention when the device of FIGS. 3 and 4 are used while no hole is present in the sheet. The vertical axis indicates the signal level, and the horizontal axis indicates the time in microseconds. The filtering consists of a deconvolution of the noise with the expected electrical signal. It can be seen from FIGS. 9 and 10 in view of FIGS. 11 and 12 that there is a quite noticeable difference between the electrical signals after filtering depending on whether there is or there is not a hole in the sheet.

Although holes are an important class of defects to be detected, other kinds of defects, such as a black spot or a light scattering defect on a transparent glass panel, can be detected with the same apparatus. In this latter case the time signal to be detected has the form of a small drop of the otherwise constant light intensity level when the opaque defect intersects the projected light beam.

Referring now to FIGS. 13 and 14, there is shown another embodiment of the inspecting apparatus for detecting the presence of a defect 2 in the sheet 4 of material. The apparatus comprises a linear array 36 of uncoupled laser diodes oriented in a direction perpendicular to the direction in which the sheet 4 moves.

The linear array of uncoupled laser diodes can be the model LP2A manufactured by Laser Diode Products (trade mark). This approach has a number of advantages as compared to a single-laser design, such as higher eye safety for a given total power. Although single diode lasers of CW power up to 1 W are available, which would produce a very intense power density along the projected line thus improving the detectability of very small pinholes, such powers are not recommended because of eye safety problems. Laser intensities higher than 1 mW/cm$^2$, if inadvertently received into the eye for durations exceeding 1 second, may exceed the maximum permissible exposure for safety. Eye hazard is related to the high collimation of a coherent laser beam, which may be focused into a very small spot on the eye retina, eventually causing hole burning and localized blindness. The use of an array of uncoupled laser emitters of relatively low power correspondingly increases the power density along the projected line while keeping the power density of each spot image in the retina of the observer at a safely low level.

The use of a linear array of uncoupled laser diodes provides spatial averaging of optical imperfections. Any dust particles, material inhomogeneities or spattered specks on the optical lenses or windows produce strong spatial modulations of the coherent laser beam diffracted by such impurities. With a single laser source, this may result in local "blind spots" along the projected laminar beam where the local light intensity falls below the required threshold power for detection of small-area pinholes. A multiple laser source produces a spatial averaging of the incoherently superposed diffraction patterns resulting in a more evenly distributed projected line intensity.

The linear array of uncoupled laser diodes provides also speckle smoothing. Coherent laser radiation scattered by particles or by an optically rough surface produces a highly contrasted speckle pattern. Again, the superposition of mutually incoherent speckle patterns from an array of uncoupled diode lasers results in a considerably smoother light distribution along the projected line. This aspect is particularly important when inspecting unpolished-surface sheets in a reflective configuration.

A low power visible light source 38 is provided for projecting a visible light beam. A dichroic mirror 40 reflects the visible light beam toward the beam shaping unit 8. The light beam is transmitted accross the dichroic mirror 40.

The low-power visible light source, such as an array of visible LED's or a lamp-illuminated slit, is collinearly superposed to the radiation from the multiple laser source through the dichroic mirror. Such mirror reflects the visible radiation and transmits the laser radiation. This is convenient for alignment purposes when the laser radiation is invisible, as it is usually the case with diode lasers emitting in the 780 to 830 nm range. A more subtle advantage of such a configuration will now be discussed in terms of eye safety. Lasers are classified in classes of increasing eye hazard in terms of their power and spectral range. Invisible radiation is considered more dangerous than visible radiation because of the possibility that a nonspecialist attendant may directly stare into the invisible beam without knowing it. If the light beam is visible, even an untrained observer will have a natural aversion to staring into an intense beam: he will instinctively blink and shift away his sight, thus avoiding long-term retina exposure to a focused laser spot.

Thus, a visible laser beam of 0.5 mW requires less precautions for on-line installation than an invisible laser beam of lower power, such as a 0.1 mW beam of 800 nm wavelength. The interest of having a collinear visible light beam of low power superposed to the near-infrared main beam is now clear: the visible light provides the required aversion to direct staring, while the near-infrared beam is convenient in terms of power, availability of rugged and cheap diode lasers, and silicon-detector sensitivity. As an example, an array of 0.8 mW, 800 nm laser diodes could be superposed to a collinear array of 0.01 mW, 600 nm LED's to obtain a visible double-wavelength beam with total power of 0.81 mW per element.

The beam shaping unit 8 comprises a first cylindrical lens 14 for converging the light beam in a direction parallel to the direction in which the sheet 4 moves as indicated by the arrow adjacent to the sheet 4. The beam shaping unit 8 also comprises a second cylindrical lens 16 for projecting the light beam in the direction substantially perpendicular to the direction in which the sheet moves. The device 18 is specifically provided for shaping the light beam into a predetermined structured light pattern.

The apparatus also comprises an optical unit 10 including a wide area lens 20 for collecting the light transmitted through the sheet 4 in a direction substantially perpendicular to the direction in which the sheet moves. A cylindrical lens 22 is provided for focusing the transmitted light onto large size detectors 42 and 46. In this embodiment, the light source 36 projects a light beam having a given wavelength. A discriminating beam splitter 44 is provided for splitting the light emitted from the surface of the sheet into first and second splitted light beams. The given wavelength being removed from the first splitted light beam by means of the discriminating beam splitter 44.

The first large area detector 42 receives the first splitted light beam and generates a first detected signal. The second large area detector 46 receives the second splitted light beam and generates a second detected signal. A signal processing system 48 subtracts the first detected signal from the second detected signal to produce an electrical signal in which the visibility of flaws is enhanced. Then the electrical signal can be filtered according to the present invention.

In an alternative embodiment, the light source 36 projects a polarized light beam. The discriminating beam splitter 44 is provided with a polarized filter so that the polarized component of the light emitted from the surface is removed from the first splitted light beam and not from the second splitted light beam.

Each detector can be a single large-area unit such as the model C30802 by RCA (trade mark) or a detector array such as the model LD20-5A by Centronic (trade mark), each detector receiving either light of different wavelength and/or of different polarization by the use of a proper optical discriminator. Examples of such discriminators would be either dichroic mirrors or polarization-dependent beam splitters. The difference between the outputs from the two detectors will only be sensitive to pinhole transmission of laser light of the proper wavelength and polarization while being insensitive to common-mode noise generated by reflections of wide-spectral-bandwidth and unpolarized ambient light variations.

The apparatus also comprises a first shielding enclosure 50 for enclosing among other things the light source 36 and the beam shaping unit 8. The first shielding enclosure 50 is provided with first 52 and second 54 apertures. The first aperture 52 is sufficiently large for permitting to the beam shaping unit to project the structured light pattern onto the sheet 4. A clean gas is injected into the second aperture 54.

The apparatus also comprises a second shielding enclosure 56 for enclosing among other things the optical unit 10 and the large area detectors 42 and 46. The second shielding enclosure 56 is provided with first 58 and second 60 apertures. The first aperture 58 is sufficiently large for permitting to the optical unit 10 to collect the light emitted from the surface of the sheet 4. A clean gas is also injected into the second aperture 60.

The shielding enclosures are added to provide convenient protection to the optical elements from the industrial environment which often contains fumes, vapor or other impurities. A constant air purge flow is injected in the enclosure producing an output flow through the slit through which the laminar light is projected on the moving sheet. A low-speed flow is sufficient to substantially reduce the requirements for periodic cleaning of the optical components, as it is well known by specialists in this field. We wish to point out that the projection of a laminar light beam is particularly well adapted to air purge requirements because the area of the output slit through which air flow must be maintained, typically a few millimeters wide, is minimized as compared to the inspection of an incoherently illuminated two-dimensional area.

Figure 16:
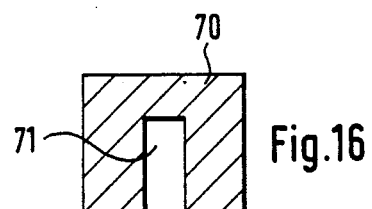
FIG. 16 illustrates in a front view the mask that is used in the apparatus shown in FIG. 15.
Figure 17:
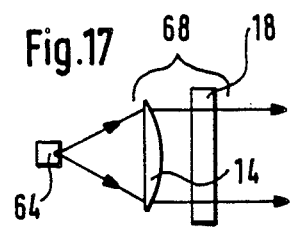
FIG. 17 is a transverse section along line 17—17' of FIG. 16.

Referring now to FIGS. 15, 16 and 17, there is shown another apparatus for detecting the presence of flaws 3 in a moving sheet 4 of material. The apparatus comprises first 62 and second 64 linear arrays of uncoupled laser diodes for projecting respectively first and second light beams. The apparatus includes first 66 and second 68 beam shaping units for shaping respectively the first and second light beams into predetermined structured light patterns. The structured light patterns, formed as laminar light beams, are projected onto a portion of the surface of the sheet 4. The two laminar light beams are coplanar. A mask 70 is provided, this mask having an aperture 71 elongated in a direction perpendicular to the plane of the laminar light beams. The apparatus also comprises a camera 72 including a line array of detecting elements for receiving the light collected by the mask 70 and generating an electrical signal indicative of the intensity of the light reflected from the portion of the surface. The detecting line array and the first and second linear arrays of uncoupled laser diodes lay in the plane of the laminar light beams.

One of the main noise sources in practical applications is the presence of ambient light. Unless the inspected material is perfectly black, ambient light reflected from the sheet adds to the background noise. As such noise is generally constant, it can be largely reduced by subtractive techniques. The approach that is proposed consists in using a memory device 74 connected to a signal processing system 76. The memory device 74 keeps in memory a continuously updated image of the light distribution across the sheet as recorded during the last few line scans. The signal processing system subtracts the newly recorded image signal from the precedent recorded image signal to enhance the visibility of the localized image features corresponding to a pinhole travelling across the field of view. Then, the signal processing system filters the resulting electrical signal with a filter having predetermined characteristics specifically adapted to match an expected electrical signal corresponding to the predetermined structured light pattern according to the present invention.

As it can be seen more specifically on FIG. 17, each beam shaping unit 66 and 68 comprises a cylindrical lens 14 for converging the light beam in a direction parallel to the direction in which the sheet 4 moves. Each beam shaping unit 66 and 68 also comprises a device 18 for specifically shaping the light beam into a predetermined structured light pattern.

This apparatus is also provided with shielding enclosures 78. Each enclosure is provided with first 80 and second 82 apertures. The first aperture 80 is sufficiently large for permitting passage of light. A clean gas is injected into the second aperture 82 of each enclosure 78.

In this case, both the camera such as the model 1902 by EGG Reticon (trade mark) and the linear array laser sources are situated on the same side of the inspected sheet which is moving in a direction perpendicular to the plane of the FIG. 15. When a surface defect intercepts the projected laminar beams, it will produce a time-dependent fluctuation of the signal detected by the detecting elements corresponding to the position of the defect on the sheet surface. The use of a multiple-laser array is particularly important in this case, because different levels of reflectivity from the light-scattering sheet surface must here be discriminated, as opposed to a faint transmitted power over a nominally zero level in the case of FIGS. 1 and 2. Random speckle-related reflectivity fluctuations must therefore be minimized to avoid false alarms, and the superposition of a large number of uncorrelated speckle patterns from an array of uncoupled diode lasers is an effective method to reduce such fluctuations.

Another important point which is illustrated in FIG. 15 is the insertion of a rectangular mask in front of the camera lens, to reduce the lens aperture in a direction parallel to the direction of the projected line on the sheet, but to extend as much as possible the aperture in the perpendicular direction. This increases the depth of field for the resolution of light fluctuations in the direction of the projected line axis while keeping the total aperture surface as large as possible for maximum light collection and for the minimization of the average speckle grain size and thus of the speckle noise. Spatial resolution in the direction perpendicular to the direction of the projected line on the sheet is assured even if the sheet wobbles out of focus because of the narrow width of the projected laminar beams.

The embodiment illustrated in FIG. 15 does not require any moving scanner, is moderately affected by speckle noise, allows each detector element to integrate the collected light intensity during a relatively long period, of the order of the line scanning time, so that the required detector speed is modest, and assures better eye safety than a single high power scanning laser. As compared to the incoherent illumination and video imaging approach discussed in the beginning of the present disclosure, the present configuration offers monochromatic laser light from which ambient light can easily be separated by optical filtering, long depth of field because of the small angular aperture of the projected laminar beam, strong laser illumination, one-dimensional scanning much faster than the readout of a two-dimensional matrix-array camera, and higher transverse resolution with a standard 2048 element line array as compared to a typically 480×550 element camera.

Although the present invention has been explained hereinabove by way of preferred embodiments thereof, it should be pointed out that any modifications to these preferred embodiments, within the scope of the appended claims are not deemed to change or alter the nature or scope of the present invention.

The embodiments of the invention in which an exclusive property or privilege is claimed are defined as follows:

1. An apparatus for detecting the presence of flaws in a moving sheet of material, comprising:
   a coherent laser light source for projecting a light beam;
   beam shaping means for shaping said light beam into a predetermined structured light pattern, and projecting said structured light pattern onto a portion of the surface of said sheet;
   optical means for collecting light emitted from said portion of said surface; light detecting means for receiving said light collected by said optical means, and generating a time-resolved electrical signal matching said predetermined structured light pattern, said signal being indicative of the intensity of said light emitted from said portion of said surface; signal processing means for filtering said electrical signal, said signal processing means having predetermined characteristics specifically adapted to match an expected electrical signal corresponding to said predetermined structured light pattern; and
   signal detecting means connected to the output of said signal processing means for detecting the presence of flaws in said sheet.

2. An apparatus as defined in claim 1, wherein said optical means collect light transmitted through said sheet when a hole is present in said sheet.

3. An apparatus as defined in claim 2, wherein said beam shaping means comprise an opaque member provided with a slit having its axis oriented parallel to the plane of said sheet, and perpendicularly to the direction in which said sheet moves.

4. An apparatus as defined in claim 2, wherein said light source is a linear array of uncoupled laser diodes oriented in a direction perpendicular to the direction in which said sheet moves.

5. An apparatus as defined in claim 1, 4 or 8, further comprising:
   a first shielding enclosure for enclosing said light source and said beam shaping means, said first shielding enclosure being provided with first and second apertures, said first aperture of said first enclosure being sufficiently large for permitting to said beam shaping means to project said structured light pattern onto said sheet, a clean gas being injected into said second aperture of said first enclosure; and a second shielding enclosure for enclosing said optical means and said light detecting means, said second shielding enclosure being provided with first and second apertures, said first aperture of said second enclosure being sufficiently large for permitting to said optical means to collect said light emitted from said surface, a clean gas being injected into said second aperture of said second enclosure.

6. An apparatus as defined in claim 1, further comprising:

a memory device connected to said signal processing means, said memory device keeping in memory an image signal corresponding to a precedent light distribution of said light emitted from said portion of said surface, said image signal being constantly updated; and wherein said signal processing means subtract a newly recorded image signal from said precedent image signal kept in memory before said filtering to enhance the visibility of localized flaws.

7. An apparatus as defined in claim 1, wherein: said light source projects a polarized light beam; said optical means comprise a discriminating beam splitter for splitting said light emitted from said portion of said surface into first and second splitted light beams, the polarized component of said light emitted from said portion of said surface being removed from said first splitted light beam by means of said discriminating beam splitter;

said light detecting means comprise a first detector for receiving said first splitted light beam and generating a first detected signal, and a second detector for receiving said second splitted light beam and generating a second detected signal; and said signal processing means subtract said first detected signal from said second detected signal to produce said electrical signal in which the visibility of flaws is enhanced.

8. A method for detecting the presence of flaws in a moving sheet of material, comprising the steps of:
 (a) projecting a laminar light beam;
 (b) shaping said light beam into a predetermined structured light pattern;
 (c) projecting said predetermined light pattern onto a portion of the surface of said sheet;
 (d) collecting light emitted from said portion of said surface;
 (e) generating an electrical signal indicative of the intensity of said light collected during said step (d);
 (f) filtering said electrical signal with a filter having predetermined characteristics specifically adapted to match an expected electric signal corresponding to said predetermined structured light pattern; and
 (g) detecting the presence of flaws in said sheet from the output signal of said filter.

9. A method as defined in claim 8, wherein said light collected during said step (d) has been transmitted through said sheet when a hole is present in said sheet.

10. A method as defined in claim 8, wherein said filtering consists of a deconvolution of said electrical signal with said expected electrical signal.

11. A method as defined in claim 8, wherein said light beam is projected by means of a linear array of uncoupled laser diodes oriented in a direction perpendicular to the direction in which said sheet moves to produce a safe, high power and low speckle noise laminar beam.

12. A method as defined in claim 8, further comprising additional steps which take place before said step (f), said additional steps including steps of:
 keeping in memory an image signal corresponding to a precedent light distribution of said light emitted from said portion of said surface;
 updating constanly said image signal; and
 subtracting a newly recorded image signal from said precedent image signal kept in memory to produce said electrical signal in which the visibility of localized flaws is enhanced.

* * * * *